(12) United States Patent  (10) Patent No.: US 7,595,872 B2
Premasiri et al.  (45) Date of Patent: Sep. 29, 2009

(54) ANALYZER FOR NANOSTRUCTURED SUBSTRATE FOR SURFACE ENHANCED RAMAN SCATTERING

(75) Inventors: W. Ranjith Premasiri, Weymouth, MA (US); Larry Ziegler, Wellesley, MA (US); Donald T. Moir, Lexington, MA (US)

(73) Assignees: Trustees of Boston University, Boston, MA (US); Microbiotix, Inc., Worcester, MA (US)

( * ) Notice: Subject to any disclaimer, the term of this patent is extended or adjusted under 35 U.S.C. 154(b) by 105 days.

(21) Appl. No.: 11/792,007

(22) PCT Filed: Dec. 5, 2005

(86) PCT No.: PCT/US2005/044010

§ 371 (c)(1), (2), (4) Date: May 31, 2007

(87) PCT Pub. No.: WO2006/065576

PCT Pub. Date: Jun. 22, 2006

(65) Prior Publication Data

US 2008/0123093 A1  May 29, 2008

Related U.S. Application Data

(60) Provisional application No. 60/632,930, filed on Dec. 3, 2004, provisional application No. 60/633,735, filed on Dec. 6, 2004.

(51) Int. Cl.
*G01J 3/44* (2006.01)
*G01N 21/65* (2006.01)

(52) U.S. Cl. .................................................. 356/301

(58) Field of Classification Search ................ 356/301
See application file for complete search history.

(56) References Cited

U.S. PATENT DOCUMENTS 5,818,047 A * 10/1998 Chaney et al. ............. 356/301
2003/0231304 A1   12/2003 Chan et al. .................. 356/301

* cited by examiner

*Primary Examiner*—F. L Evans
(74) *Attorney, Agent, or Firm*—Weingarten, Schurgin, Gagnebin & Lebovici LLP

(57) ABSTRACT

A Raman scattering spectrographic analyzer wherein a microscope objective is adapted to view single bio-specimens on a substrate having monodispersed-sized metal particles. A defined wavelength of radiation is applied through the microscope and returning radiation resulting from Raman scattering by bio-specimens is applied to a spectrometer operative to provide a signal corresponding to the wavelength components in said Raman scattered or shifted radiation. The spread spectrum of the Raman shift is analyzed for identification of a bio-specimen.

21 Claims, 16 Drawing Sheets

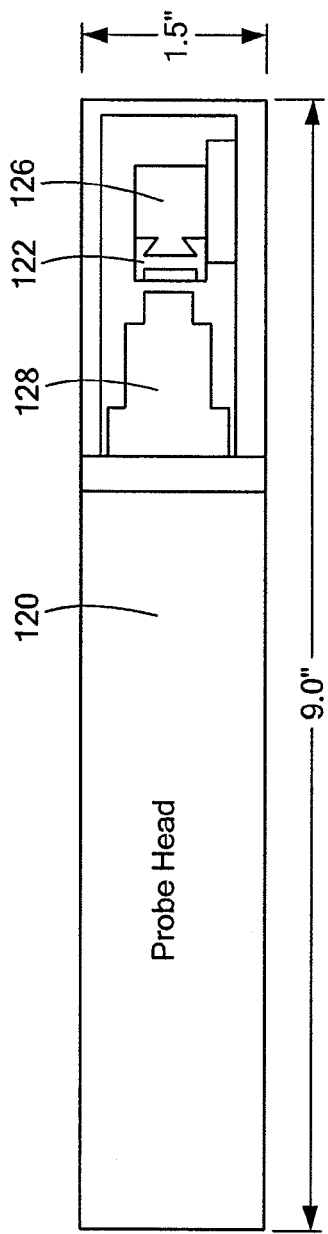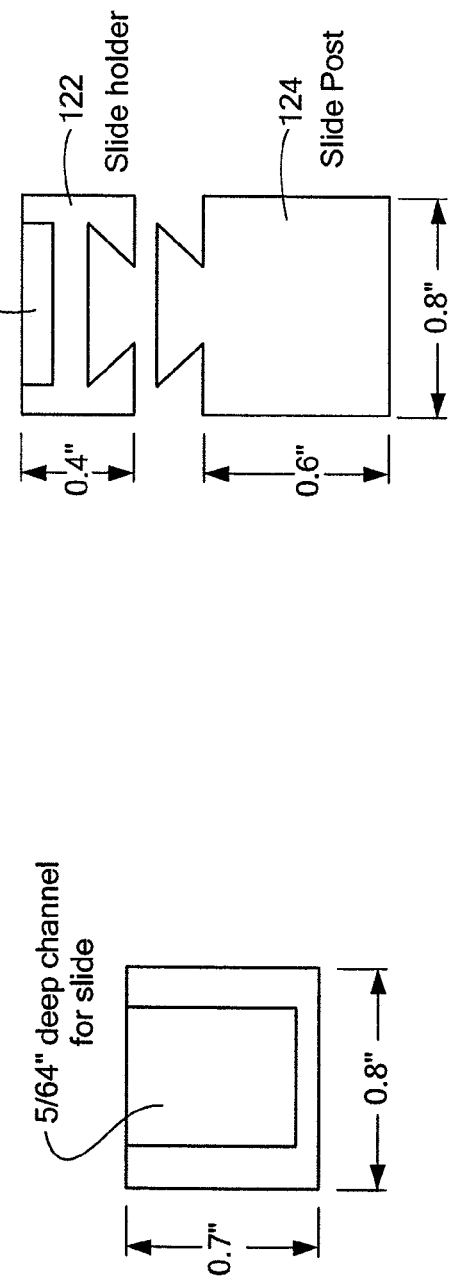
*FIG. 16 (a)*
*FIG. 16 (b)*
*FIG. 16 (c)*

ANALYZER FOR NANOSTRUCTURED SUBSTRATE FOR SURFACE ENHANCED RAMAN SCATTERING

CROSS REFERENCE TO RELATED APPLICATIONS

This application claims the priority of U.S. Provisional Application No. 60/632,930 filed Dec. 3, 2004 and entitled, SEEDED DEPOSITION OF METAL NANO-CLUSTERS USING NANO-PARTICLES ON A SOLID MATRIX, and U.S. Provisional Application No. 60/633,735 filed Dec. 6, 2004 and entitled, SEEDED DEPOSITION OF METAL NANO-CLUSTERS USING NANO-PARTICLES ON A SOLID MATRIX, which are hereby incorporated by reference herein.

BACKGROUND OF THE INVENTION

The fields of nanoscience and nanotechnology generally concern the synthesis, fabrication and use of nanoparticles and nanostructures at atomic, molecular and supramolecular levels. The nanosize of these particles and structures offers potential for research and applications across various scientific disciplines such as materials science, engineering, physics, chemistry, spectroscopy, computer science, microscopy and biology. For example, surfaces or substrates employing nanostructures can be used to enhance Raman scattering by many orders of magnitude, an effect often referred to as surface enhanced Raman scattering (SERS).

SERS is a common spectroscopic technique that can be used for detecting and identifying biological molecules. Typically, unique vibrational signatures or fingerprints can be observed for biological molecules via SERS. In aqueous media, the ability to rapidly produce such a vibrational signature for a biological molecule lacking visible chromophores demonstrates the potential of SERS as a valuable analytical and structural spectroscopic technique particularly for samples of low concentrations. Recent SERS applications and developments have also been extended toward the detection and identification of bacterial and viral pathogens. To date, conventional surfaces or substrates for SERS have been largely unsuccessful in reproducibly and reliably detecting and identifying such pathogens.

SUMMARY OF THE INVENTION

The present invention provides a Raman scattering analyzer employing a nanostructured substrate for enhanced Raman scattering. The Raman scattering spectrographic analyzer has a microscope objective adapted to view bio-specimens on a substrate having monodispersed-sized metal particles. The microscope stage can be spatially scanned automatically so that image recognition software can be used to identify specific pathogens in the field of view for SERS measurements. A defined wavelength of radiation is applied through the microscope and returning radiation resulting from Raman scattering by bio-specimens is directed to a spectrometer operative to provide a signal corresponding to the wavelength components in said Raman scattered or shifted radiation. The dispersed SERS spectrum of the Raman shift is analyzed for identification of a bio-specimen.

A substrate for use in the invention comprises a surface featuring substantially monodisperse-sized metal nanoparticles disposed thereon. Preferably, the substrate surface provides for enhanced Raman scattering and spectra therefrom. For example, a nanostructured substrate of the invention can be used to reproducibly and reliably detect or identify bacterial and viral pathogens. A substrate of the invention overcomes the shortcomings of conventional surfaces or substrates such as those described above. Furthermore, the combination of this substrate and the near diffraction limit of the optical elements of this analyzer allow single bacterial cells to be detected and identified.

DESCRIPTION OF THE DRAWINGS

Other features and advantages of the invention may also be apparent from the following detailed description thereof, taken in conjunction with the accompanying drawings of which:

FIG. 6 shows SERS spectra of *B. anthracis* Sterne provided via nanostructured substrates of the invention;

FIG. 10 shows a SERS spectrum of a two-cell chain of *B. anthracis* Sterne compared to a SERS spectrum resulting from multiple cells yielded via a nanostructured substrate of the invention;

FIG. 11 shows SERS spectra as a function of growth time for *B. anthracis* Sterne cells obtained from a nanostructured substrate of the invention;

FIG. 12 shows SERS spectra for *Bacillus thuringiensis* (*B. thuringiensis*) and *B. anthracis* Sterne after admixing with human heparinized serum provided via a nanostructured substrate of the invention;

FIG. 13 (*a*) shows SERS spectra for *B. subtilis* spores produced by using a nanostructured substrate of the invention;

FIG. 13 (*b*) shows SERS spectra of the supernatant from culture medium containing bovine viral diarrhea virus particles and a SERS spectrum for the corresponding culture medium supernatant of non-infected cells obtained via a nanostructured substrate of the invention;

FIG. 14 is a generalized block diagram of a Raman analyzer of the invention;

FIG. 15 is a detailed diagram of the analyzer of FIG. 14; and

FIGS. 16*a*-16*d* are diagrams of a portable embodiment;

FIGS. 17*a* and 17*b* are respective diagrams and pictorial views of a modified version of the portable unit of FIGS. 16*a*-16*b*; and

Figure 18:
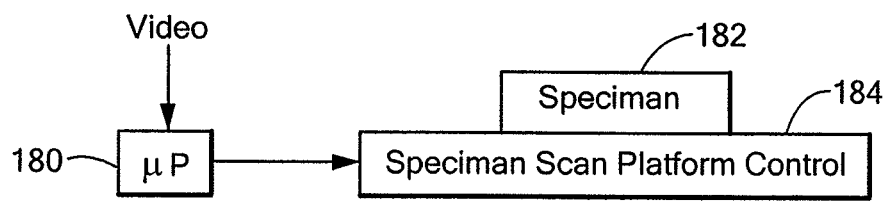

FIG. 18 is a diagram of a character recognition option for the invention.

DEFINITIONS

Unless otherwise stated, the following definitions provide meaning and examples to terms used herein. Such definitions are also intended to encompass any meaning that may be contemplated by a person of ordinary skill within the art.

The terms "monodisperse" or "monodisperse-sized" and derivations thereof such as substantially monodisperse-sized generally refer to substantially uniformly or homogeneously proportioned or sized particles such as metal nanoparticles. For example, metal nanoparticles for a nanostructured substrate of the invention can be physically distinguishable from particles within conventional surfaces or substrates for SERS as these nanoparticles are substantially uniformly or homogeneously proportioned or sized.

DETAILED DESCRIPTION OF THE INVENTION

The present invention provides a nanostructured substrate for SERS. A substrate of the invention comprises a surface featuring substantially monodisperse-sized metal nanoparticles disposed thereon. In one embodiment, a nanostructured substrate of the invention comprises a surface featuring metal nanoparticles substantially aggregated in clusters. Exemplary metal nanoparticles disposed on the substrate surface can be silver, gold, copper or combinations thereof. Preferably, metal nanoparticles disposed on a substrate surface can be substantially spheroidal. A substrate surface can also comprise silicon dioxide, aluminum oxide, titanium dioxide or combinations thereof.

The invention also provides methods for syntheses or uses of a nanostructured substrate comprising monodisperse-sized metal nanoparticles disposed on a surface thereof. In one embodiment, a method of the invention can be performed to obtain a nanostructured substrate comprising monodisperse-sized metal nanoparticles. For example, the method can comprise growing substantially monodisperse-sized metal nanoparticles on the substrate surface. Preferably, a method of the invention is also performed to detect or identify an entity. The method can comprise performing Raman microscopy of the entity to produce a SERS spectrum thereof.

Figure 1:
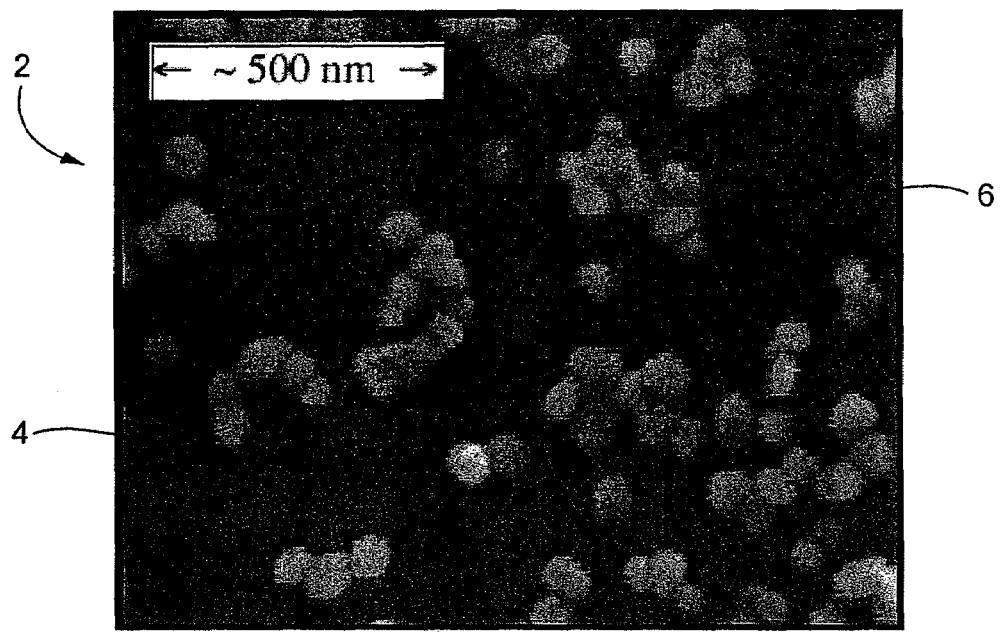
FIG. 1 shows a scanning electron microscopy (SEM) image of an exemplary nanostructured substrate of the invention.

FIG. 1 shows an SEM image of an exemplary nanostructured substrate of the invention. As shown, the substrate 2 comprises substantially monodisperse-sized gold nanoparticles 4 disposed on a surface 6 thereof. The substrate 2 and surface 6 of FIG. 1 comprise silicon dioxide. The monodisperse-sized gold nanoparticles 4 are substantially spheroidal comprising diameters in a range from about 40 to 120 nm. FIG. 1 shows the gold nanoparticles 4 as substantially aggregated in clusters. Exemplary clusters for a substrate of the invention can comprise from about 2 to 25 metal nanoparticles.

Figure 2:
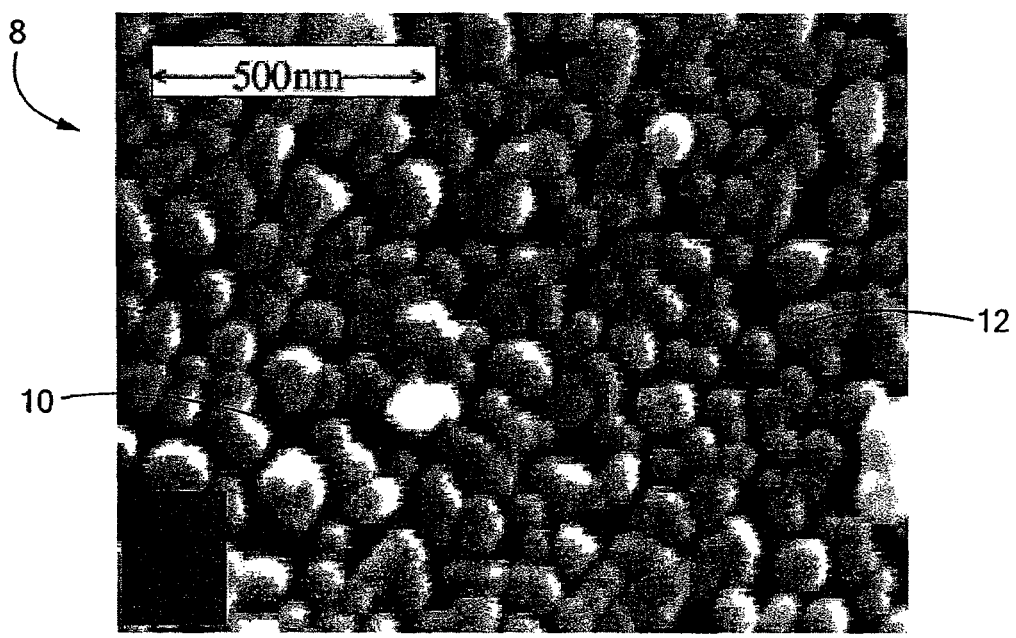
FIG. 2 shows an SEM image of an exemplary nanostructured substrate of the invention.

FIG. 2 shows an SEM image of an exemplary nanostructured substrate of the invention. As shown, the substrate 8 comprises substantially monodisperse-sized silver nanoparticles 10 disposed on a surface 12 thereof. The substrate 8 and surface 10 of FIG. 2 comprise silicon dioxide. Exemplary substrates of the invention can comprise silicon dioxide, aluminum oxide, titanium dioxide or combinations thereof. The monodisperse-sized silver nanoparticles 10 in FIG. 2 are substantially aggregated in clusters. Exemplary metal nanoparticles for a substrate of the invention can comprise silver, copper, gold or combinations thereof.

The surface topology or morphology of exemplary substrates such as shown in FIGS. 1 and 2 can affect SERS and spectra therefrom. For example, the substantially monodisperse-sized gold nanoparticles in FIG. 1 can feature a lower gold nanoparticle density on or along the substrate surface than the silver nanoparticles of FIG. 2. In one embodiment, monodisperse-sized metal nanoparticles such as silver can substantially or entirely cover or coat a nanostructured substrate surface. Exemplary monodisperse-sized silver nanoparticles for a substrate of the invention can be substantially spheroidal having diameters in a range from about 40 to 120 nm.

SERS and spectra therefrom via a substrate of the invention can be comparable for different types of nanoparticles, although vibrational signatures of an entity are generally metal dependent. Vibrational signature metal dependence for a substrate can be related to different surface topologies or morphologies. In addition, vibrational signature metal dependence can also be related to the chemical properties of the nanoparticles disposed on the substrate surface. Preferably, a substrate of the invention can provide for SERS spectra of bacterial or viral pathogens. A nanostructured substrate can also yield SERS spectra of chemical or biological molecules.

For example, a substrate of the invention provides for a Raman cross-sectional enhancement of about $5 \times 10^7$ for glycine at an excitation of 785 nm.

Figure 3:
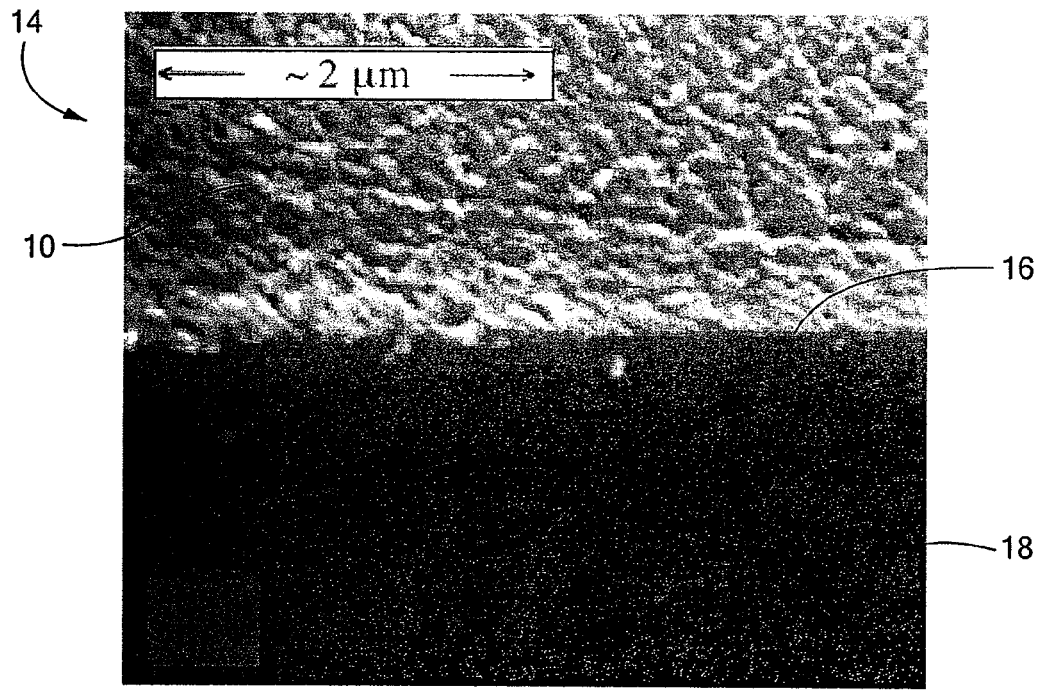
FIG. 3 shows an SEM image of a cleaved nanostructured substrate of the invention.

FIG. 3 shows an SEM image of a cleaved nanostructured substrate of the invention. The substrate 14 is oriented to show a surface 16 and interior 18 thereof. As shown, monodisperse-sized gold nanoparticles 20 are substantially disposed on the surface 16 of the substrate 14. The gold nanoparticles 20 are also shown substantially covering or coating the substrate surface. The substrate 14 and surface 16 shown in FIG. 3 also comprise silicon dioxide.

Figure 4:
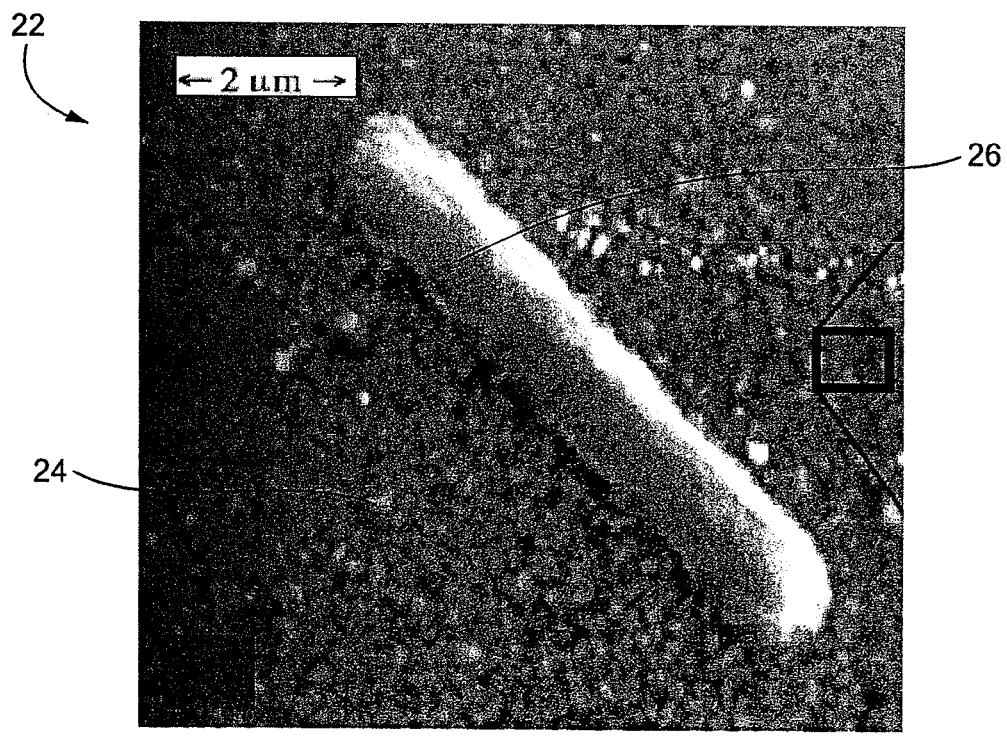
FIG. 4 shows an SEM image of a nanostructured substrate of the invention comprising an entity in contact with substantially monodisperse-sized gold nanoparticles.

In one embodiment, a substrate of the invention comprises an entity substantially disposed on a surface thereof. The substrate surface also comprises monodisperse-sized metal nanoparticles. FIG. 4 shows an SEM image of an exemplary nanostructured substrate of the invention comprising an entity in contact with substantially monodisperse-sized metal nanoparticles. As shown, the substrate 22 comprises monodisperse-sized gold nanoparticles 24. Moreover, the entity 26 in FIG. 4 is a single two-cell chain of *B. anthracis* Sterne disposed on the substrate surface. The entity 26 disposed on the substrate 22 is in contact with one or more of the gold nanoparticles 24.

Exemplary entities for a substrate of the invention can include spores, pathogens, fluids, cells, amino acids, biological materials, molecules, nucleic acids, tissue samples, viruses, bacteria, inorganic materials, serums, vegetative samples, germinating samples, sputum, human blood, bronchoalveolar lavage fluid, cerebral spinal fluid or combinations thereof. In one embodiment, a nanostructured substrate can provide for SERS and spectra therefrom, which are unique to an entity. Preferably, the entity can be in contact with one or more monodisperse-sized metal nanoparticles substantially disposed on the substrate surface.

The examples herein are provided to illustrate advantages of the invention that have not been previously described. The examples are also intended to assist a person of ordinary skill within the art in syntheses and uses of a nanostructured substrate of the invention. The examples can incorporate or otherwise include any variations or inventive embodiments or aspects as described above. The embodiments described above can also incorporate or otherwise include any variations or inventive embodiments or aspects of the examples herein. The examples are also not intended in any way to limit or otherwise narrow the disclosure or scope thereof as generally provided herein.

EXAMPLES

Exemplary Syntheses of Substrates of the Invention

Exemplary syntheses of nanostructured substrates of the invention were performed via in situ growth methods. For example, a gold ion doped sol-gel was formed by hydrolysis of tetramethoxysilane ($Si(OCH_3)_4$) in an acidic (about 0.005 milliliters (ml) of about 1 percent (%), volume per volume, concentration of hydrochloric acid (HCl)) methanol solution (about 10 ml of high performance liquid chromatography (HPLC) grade methanol, about 5 ml of water and about 3 ml of $Si(OCH_3)_4$ 99.99% from Sigma-Aldrich, St. Louis, Mo. 63103) of metal precursors such as chlorauric acid ($HAuCl_4$) (about 50 microliters (μl) of about 1 molar (M) $HAuCl_4$ from Sigma-Aldrich) based metal precursors.

After about 3 hours of agitation to complete hydrolysis, sol-gel aliquots (about 25 μl) within microcentrifuge tubes, such as polypropylene microcentrifuge tubes, were dried in a fume hood for about 12 to 48 hours at ambient temperature and airflow (relative humidity about 40%). The resulting matrixes of gel pellets or chips comprising metal precursors were then exposed to water saturated air for about 1 hour. These gel pellet or chip matrixes were vigorously agitated (about 30 seconds) with about 0.66 millimolar (mM) of a reducing agent such as an aqueous sodium borohydride (99.99% from Sigma-Aldrich) solution in a first reduction step. The first reduction step rapidly reduced the metal precursors in the matrixes providing gold seeds for substantially monodisperse-sized metal nanoparticle surface growth during a second reduction step.

The solution was drained and about 50 ml of water were added to the gel pellet or chip matrixes. Gentle agitation was then induced for about 30 minutes to form silicon dioxide substrates from the matrixes for monodisperse-sized metal nanoparticle growth thereon. For the second reduction step, these substrates remained in a low concentration of a reducing agent for about 24 hours. The second reduction step slowly reduced the metal precursors to grow monodisperse-sized gold nanoparticles substantially on an exposed outer surface of the substrate, yielding an exemplary nanostructured substrate of the invention such as shown in FIG. 3.

To aid in consistent syntheses of nanostructured substrates of the invention, ambient airflow can also be filtered via a hydrocarbon absorbing filter and 300 micron (μ) particulate filters. The exemplary nanostructured substrates of the invention provide for SERS. The invention also contemplates performing exemplary syntheses or variations thereof to yield substantially monodisperse-sized metal nanoparticles other than gold. For example, given syntheses can be varied to produce monodisperse-sized silver nanoparticles substantially disposed on a substrate of the invention by substituting silver nitrate ($AgNO_3$) for $HAuCl_4$, limiting the first reduction step to about 5 seconds and employing about a five-fold lower reducing agent concentration.

Exemplary syntheses of a nanostructured substrate can also be varied by manipulating metal precursor or reducing agent concentrations. Moreover, adjusting relative humidity during syntheses can yield low or high densities of substantially monodisperse-sized metal nanoparticles. For example, a low density of monodisperse-sized metal nanoparticles can partially cover or coat a surface for a nanostructured substrate of the invention. By comparison, a high density of monodisperse-sized metal nanoparticles can substantially or entirely cover or coat a substrate surface. Such variations to exemplary syntheses for a substrate of the invention can also affect Raman cross-sectional enhancement including SERS intensities.

Nanostructured substrates produced by exemplary syntheses can also feature monodisperse-sized metal nanoparticles substantially aggregated in clusters. For example, monodisperse-sized gold nanoparticles were substantially disposed on substrates comprising silicon dioxide, partially covering or coating outer surfaces thereof. In contrast to nanostructured substrates of the invention, conventional surfaces or substrates for SERS consist of metal particles or colloids embedded or dispersed therein.[1] Metal particles embedded within conventional surfaces or substrates also tend to be nonuniformly or inhomogeneously proportioned and sized.[2]

Exemplary Uses of Substrates of the Invention

Exemplary uses for nanostructured substrates include providing for SERS of entities such as bacterial or viral pathogens. A nanostructured substrate can also provide for SERS of chemical or biological molecules. To demonstrate SERS of bacterial pathogens, E. coli, S. typhimurium, Bacillus cereus (B. cereus), B. anthracis Sterne and B. thuringiensis samples were obtained from Carolina Biological Supply, Burlington, N.C. 27215. Bacillus subtilis (B. subtilis) YS11 was also obtained from the Bacillus Genetic Stock Center (BGSC), Columbus, Ohio 43210.

In addition, B. subtilis 3610 (SSB2) and its congenic insertion deletion construct hag: :erm (SSB71) were provided by the Department of Microbiology and Molecular Genetics, Harvard Medical School, Boston, Mass. 02115. A B. anthracis Sterne cotE: :cat mutant was also provided by the Department of Microbiology and Immunology, Loyola University Medical Center, Chicago, Ill. 60153. The in vitro bacterial pathogen samples were grown in about 5 ml of Luria-Bertani (LB) broth (about 5 hours) to an OD600 equal to about 1. The samples were then washed five times with water and resuspended in about 0.25 ml of water.

A platinum loop was used to place about 1 μl of a bacterial pathogen sample suspension on an nanostructured substrate of the invention. SERS spectra were generally acquired within minutes after placing the samples on the substrate surface comprising substantially monodisperse-sized metal nanoparticles. Bulk Raman spectra of bacterial pathogen samples, excited with about 300 milliwatts (mW) at about 785 nm, were correspondingly placed on a standard potassium bromide (KBr) material. A Renishaw Raman microscope (model RM2000) capable of about 2λ spatial resolution was used for measurements at about 785 nm (diode laser excited).

Typically, SERS spectra of bacterial pathogen samples on a nanostructured substrate of the invention were obtained with an incident laser power at about 1 to 3 mW and spectral acquisition time of about 10 seconds. An exemplary spectral resolution was set to about 3 $cm^{-1}$ for a cooled charged coupled device (CCD) (400×578 array size) detection system (0.25 meter (m) spectrometer fitted with a 1200 groove per millimeter (mm) grating). A 520 $cm^{-1}$ vibrational band of a silicon wafer provided frequency calibration. Several microscope objectives including about 50 and 100 times (×) objectives were used for excitation and collection.

Figure 5:
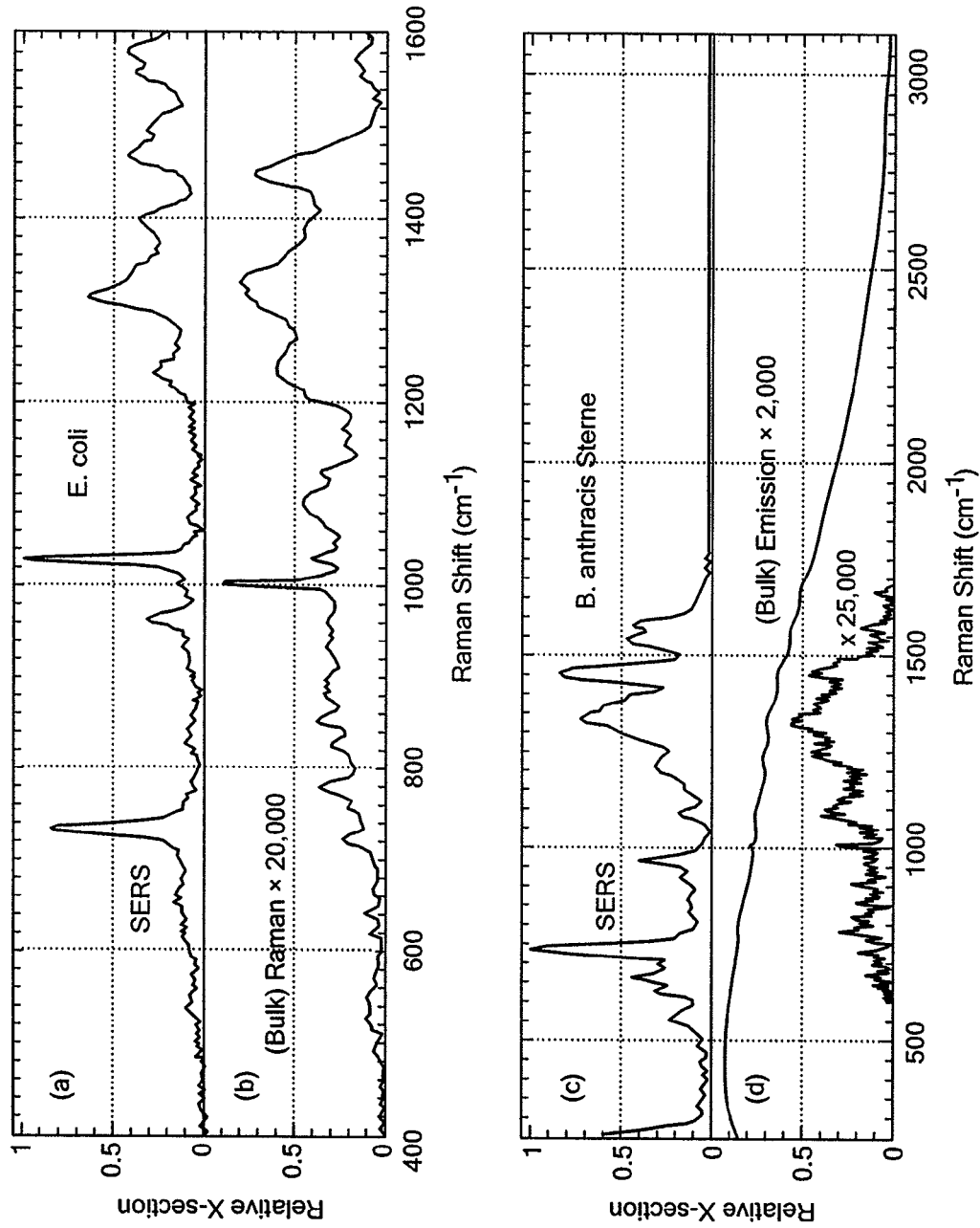
FIG. 5 shows SERS and bulk Raman (non-SERS) spectra for Gram-negative *Escherichia coli* (*E. coli*) and Gram-positive *Bacillus anthracis* Sterne (*B. anthracis* Sterne)

FIG. 5 shows SERS and bulk Raman spectra for Gram-negative E. coli and Gram-positive B. anthracis Sterne bacteria. The relative scattered power per bacterium of the SERS and bulk Raman spectra of E. coli and B. anthracis Sterne, normalized for incident laser power, sample concentration and data collection times are shown in FIG. 5. The SERS spectra in FIG. 5 were obtained from monodisperse-size gold nanoparticle covered substrates of the invention. As shown, the spectrum of E. coli was amplified by a factor of $2\times10^4$ per bacterium when comparing the intensities of the strongest vibrational band of the SERS and bulk Raman spectra.

Correspondingly, Raman cross-sectional enhancement per B. anthracis Sterne bacterium was about $5\times10^4$ due to the gold nanoparticles of the substrate. The greater amplification factor for B. anthracis Sterne as compared to E. coli may be attributable to different Gram-positive and Gram-negative cell surface structures of these two types of bacterial pathogens. About 300 mW of incident 785 nm excitation power and 100 second signal accumulation times were used to obtain the bulk Raman spectra of FIG. 5. By comparison, the SERS spectra were excited with about 2 mW and collected in about 10 seconds.

The bulk Raman spectrum of B. anthracis Sterne excited at 785 nm was dominated by broad fluorescence as shown by spectrum (d) in FIG. 5. A relatively weak and noisy spectrum can also be identified overlapping the broad fluorescence of the bulk Raman B. anthracis Sterne emission. In contrast, only a strongly enhanced emission, lacking the broad fluorescence feature, was evident for the SERS spectrum of B. anthracis Sterne produced via a nanostructured substrate comprising substantially monodisperse-sized gold nanoparticles disposed on a surface thereof.

Figure 6:
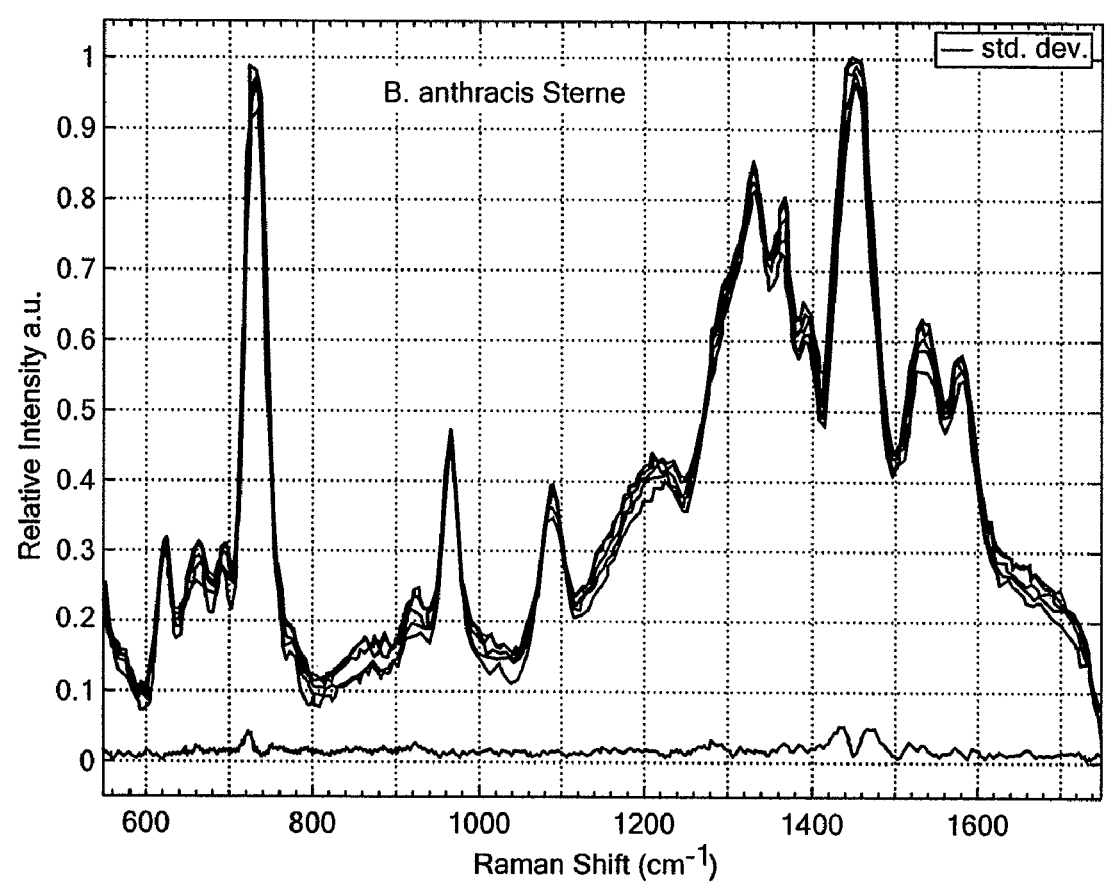

FIG. 6 shows six SERS spectra of B. anthracis Sterne obtained from nanostructured substrates of the invention. The spectra were observed at three separate locations on a substrate surface, and from three different substrates of the invention each of which featuring substantially monodisperse-sized gold nanoparticles. Each spectrum was normalized by the intensity of the strongest band thereof. A corresponding standard deviation spectrum is also shown in FIG. 6.

The absolute scattering intensities of these spectra varied by less than about 15% at about 735 $cm^{-1}$ (signal maximum). These spectra were typical of samples from the same B. anthracis Sterne culture or cultures grown on different days in a common broth type. The spectra in FIG. 6 demonstrate the reproducibly and reliably of detecting and identifying bacterial pathogens via nanostructured substrates of the invention. By comparison, conventional metal particle embedded surfaces or substrates and colloids dispersed in solution for SERS are often irreproducible and, as a result, unreliable for routinely detecting and identifying such pathogens via SERS.[3]

Figure 7:
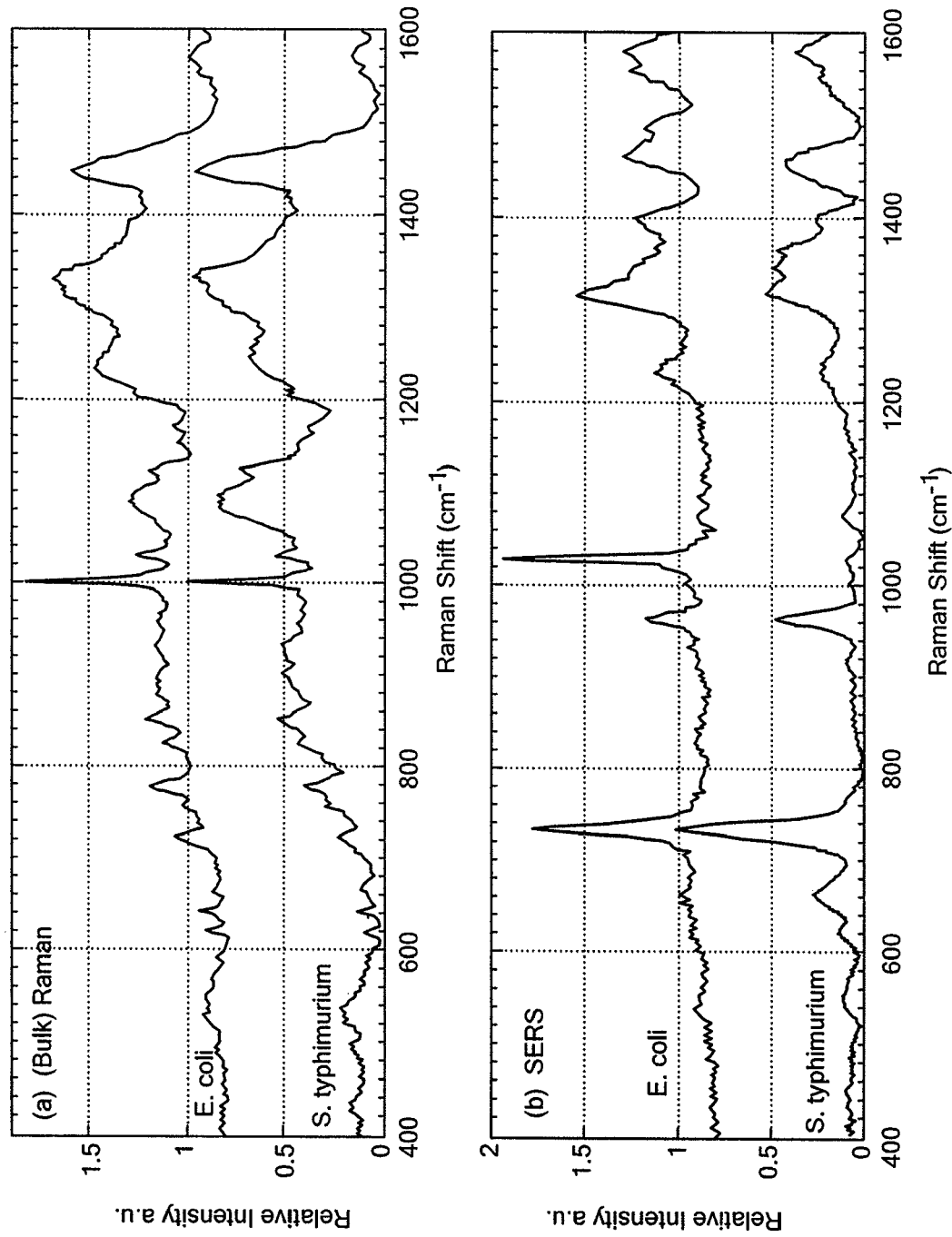
FIG. 7 shows SERS and bulk Raman spectra for *E. coli* and *Salmonella typhimurium* (*S. typhimurium*)

FIG. 7 shows SERS and bulk Raman spectra for two phylogenetically related species, E. coli and S. typhimurium. As shown, the bulk Raman spectra of these two bacterial pathogens were extremely similar judging by the peak positions and relative intensities of the observed emission bands in spectra (a) of FIG. 7. To contrast, SERS spectra of E. coli and S. typhimurium on nanostructured substrates of the invention shown by spectra (b) in FIG. 7 exhibited much more distinct vibrational features than the bulk Raman spectra. For example, the relative intensity of a 1050 $cm^{-1}$ band and relative intensity patterns in the 1200 to 1700 $cm^{-1}$ region were obvious spectral differences in the SERS spectra of E. coli and S. typhimurium obtained from a substrate of the invention. As a result, the greater spectral discrimination observed in the SERS spectra from nanostructured substrates of the invention allow more accurate and faster species detection and identification than conventional Raman or infrared (IR) absorption techniques.

In addition to enhanced species vibrational specificity, the number of transitions in the SERS spectra of E. coli and S. typhimurium via a substrate of the invention were significantly fewer than in corresponding bulk Raman spectra. FIG. 7 also shows that SERS spectra obtained from a substrate of the invention exhibited reduced vibrational spectral congestion relative to bulk Raman spectra. Such simplified and more species distinct vibrational signatures using a substrate comprising substantially monodisperse-sized metal nanoparticles provides a spectroscopic technique surpassing the capabilities of conventional Raman or IR absorption techniques.

Figure 8:
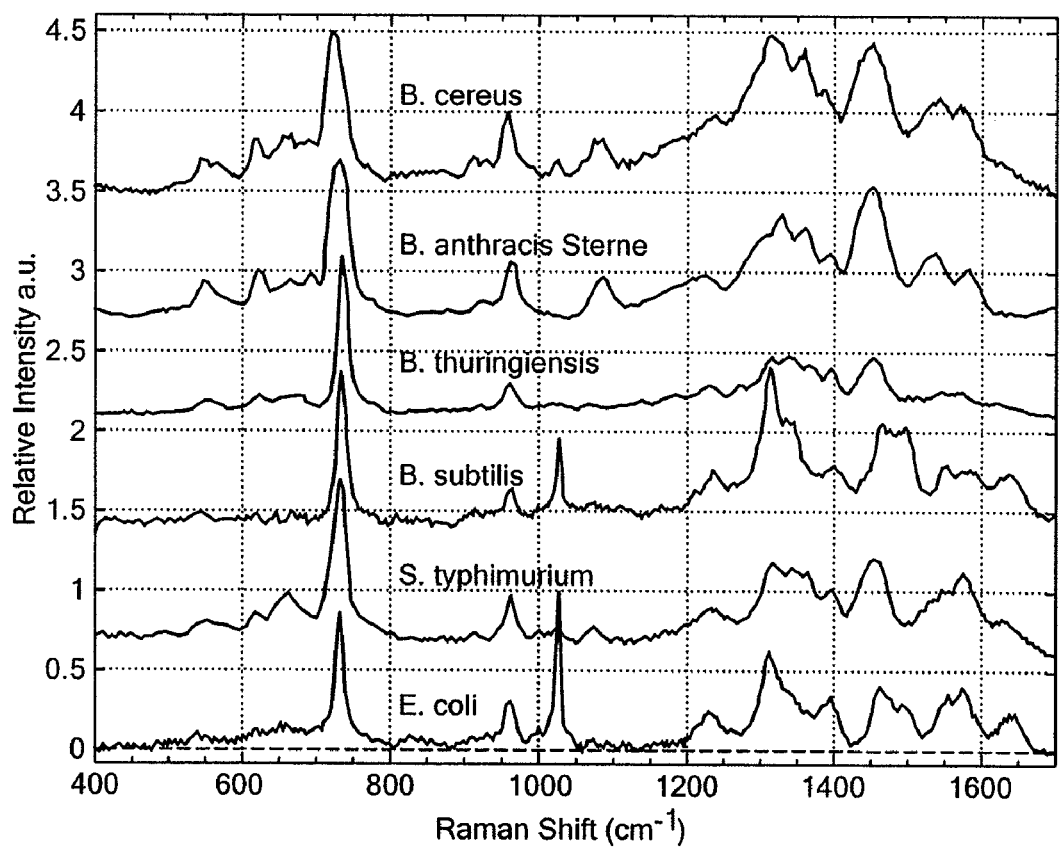
FIG. 8 shows SERS spectra for several bacterial pathogens produced by using a nanostructured substrate of the invention.

FIG. 8 shows SERS spectra for several bacterial pathogens yielded from a nanostructured substrate of the invention. These spectra resulted from the scattering of about 25 to 100 vegetative bacterial cells, depending on the bacterial pathogen, illuminated by about 2 mW of incident 785 nm laser power for an accumulation time of about 10 seconds. The spectra were corrected for the spectral response of the system and some baseline effects. Additional averaging or smoothing was not applied to the spectra. The spectra of FIG. 8 demonstrated that SERS spectra produced via a nanostructured substrate of the invention can display excellent signal to noise for vegetative bacterial cells excited by low laser power radiation at about 785 nm.

Additionally, the spectra of FIG. 8 demonstrated that SERS spectra produced via a nanostructured substrate of the invention can provide reproducible and reliable vibrational signatures specific to a bacterial pathogen. The invention also contemplates obtaining vibrational signatures for any suitable entity using a substrate comprising substantially monodisperse-sized metal nanoparticles. In one embodiment, these signatures can comprise a vibrational signature library for reproducible and reliable entity detection or identification.

For example, a vibrational signature library of the invention can be maintained on a system comprising a processor such as computer. Such a computer can also comprise algorithms or instructions that are stored in memory and executed by the processor for the detection or identification of an entity by using a substrate of the invention for SERS. The invention also contemplates that exemplary algorithms or instructions can be performed by a processor executing scripts, compiled programs or any other suitable components such as downloadable applets or plug-ins. Furthermore, a vibrational signature library can be stored on firmware, hardware, software or combinations thereof such as combinatorial logic, integrated circuits or gate arrays.

Using a nanostructured substrate of the invention for SERS, bacterial pathogen strains and mutants can also be distinguished based on unique vibrational signatures. For example, SERS spectra for a B. subtilis congenic mutant lacking flagella hag: :erm and B. subtilis strains, YS11 and 3610, exhibited distinct vibrational signatures using a nanostructured substrate of the invention. These spectra demonstrated that a nanostructured substrate can provide a reproducible and reliable basis for detection or identification of closely related species of bacterial pathogens.

Figure 9:
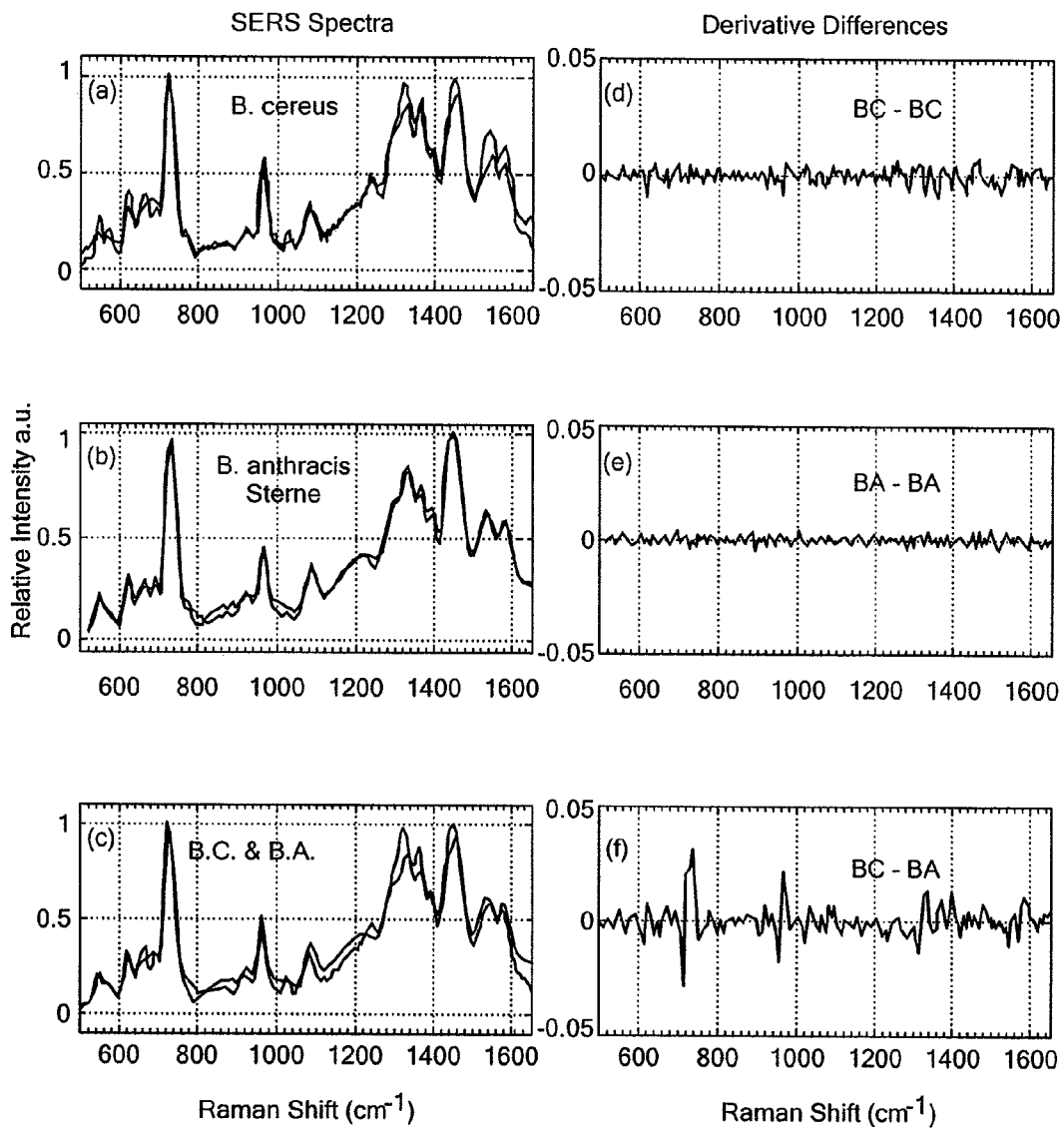
FIG. 9 shows SERS spectra for two closely related species of bacterial pathogens obtained via a nanostructured substrate of the invention.

Additional evidence for the ability of a nanostructured substrate of the invention to provide species specific vibrational signatures for detection and identification of bacterial pathogens is demonstrated by FIG. 9. FIG. 9 shows SERS spectra for two very closely related bacterial pathogen species, B. cereus and B. anthracis Sterne, produced by using a substantially monodisperse-sized gold nanoparticle covered substrate of the invention. These spectra are shown as spectra (a), (b) and (c). Moreover, derivative difference spectra of B. cereus and B. anthracis Sterne, spectra (d) and (e) of FIG. 9, demonstrated signal reproducibility achievable via nanostructured substrates of the invention. The derivative difference spectrum between *B. cereus* and *B. anthracis* Sterne, spectrum (f) of FIG. 9, also demonstrated the ability of SERS spectra from substrates of the invention to provide distinct spectral distinctions between two species that can be used for detection and identification purposes. The invention also contemplates alternative uses for a substrate comprising monodisperse-sized metal nanoparticles based on these species specific SERS spectra.

Figure 10:
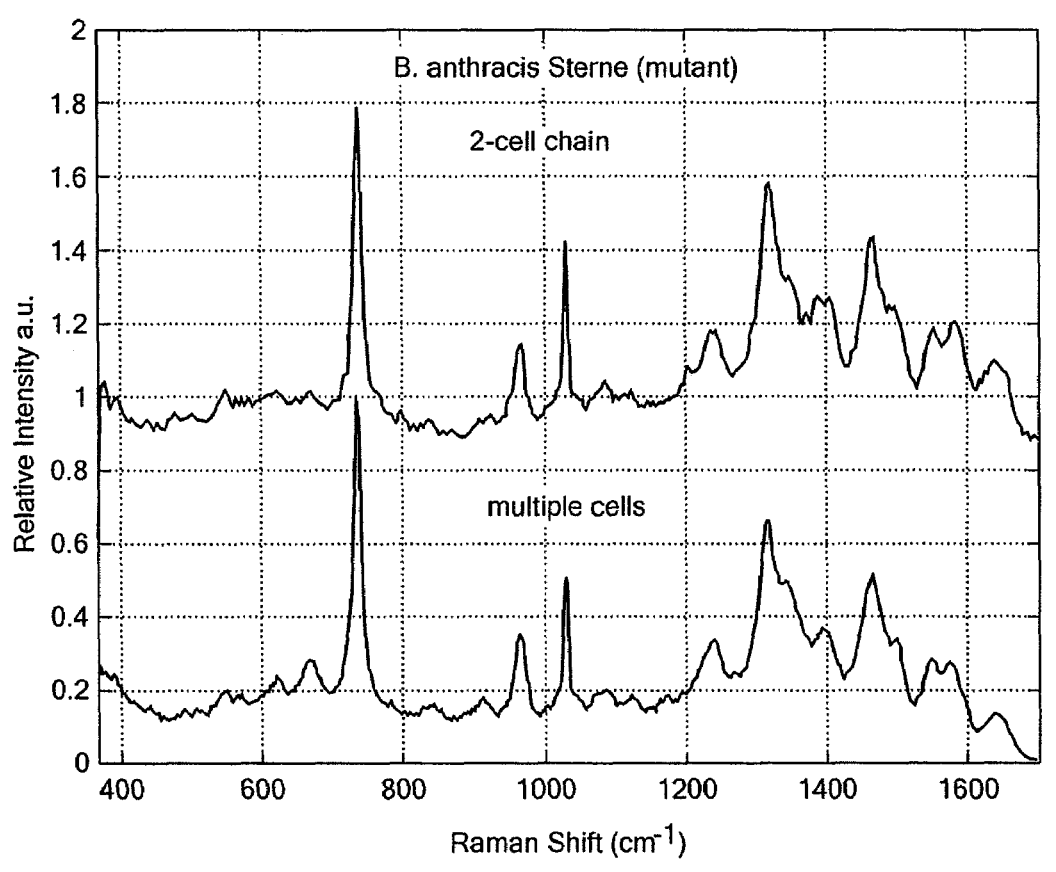

As an example of single cell capability for a substrate of the invention, SERS spectrum of a *B. anthracis* Sterne (cotE::cat) mutant two-cell chain was detected and identified. In particular, FIG. 10 shows a SERS spectrum of a two-cell chain of *B. anthracis* Sterne compared to a SERS spectrum resulting from multiple cells yielded via a nanostructured substrate of the invention comprising monodisperse-sized gold nanoparticles. A white light image at the laser focal region confirmed that only a single bacterium was in the illuminated volume during detection and identification. A 100× objective and 20 seconds of 3 mW of 785 nm incident laser power were used to observe the single cell level spectrum of FIG. 10.

The SERS spectrum of multiple *B. anthracis* cells (about 30 cells) was also obtained with less tightly focused excitation (50× objective and about 10 seconds for data accumulation). In addition to enabling bacterial pathogen mixture identification, single cell detection capabilities for a substrate of the invention can minimize the effects of spectral contamination in the SERS of biological fluids such as a fluid comprising an entity of interest. Moreover, spectral contributions from non-bacterial components of in vivo derived samples can be greatly reduced as a result of the ability to observe vibrational signatures from a bacterium filled sampling volume.

Figure 11:
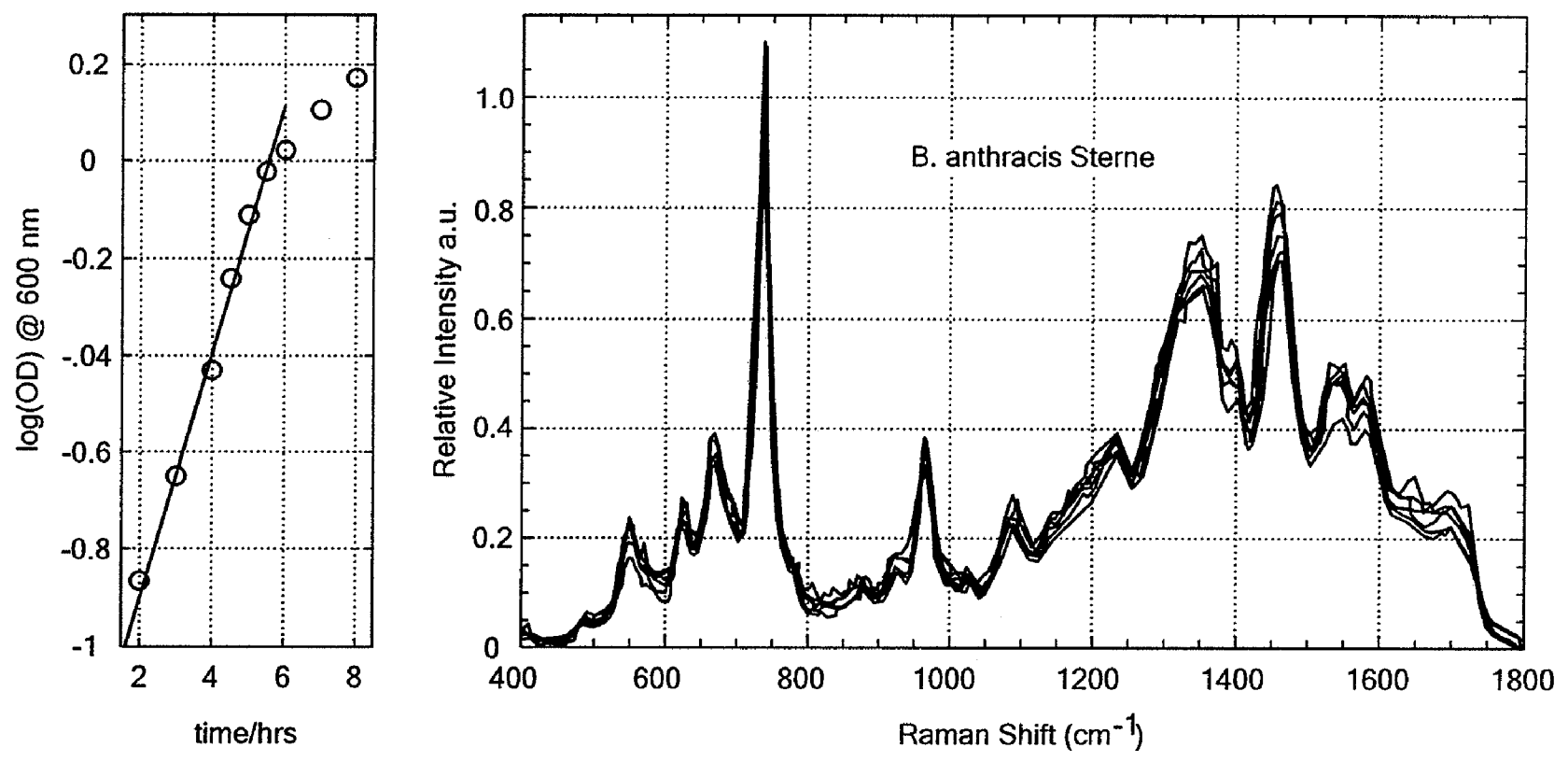

FIG. 11 shows SERS spectra for *B. anthracis* Sterne cells obtained from a nanostructured substrate of the invention acquired for cells harvested seven times during the course of bacterial culture growth. The spectra from each of these times through the growth cycle were demonstrated to be nearly identical to one another. By using a nanostructured substrate of the invention for SERS and spectra therefrom, only minimal surface changes were detectable in the life cycle of the culture.

Figure 12:
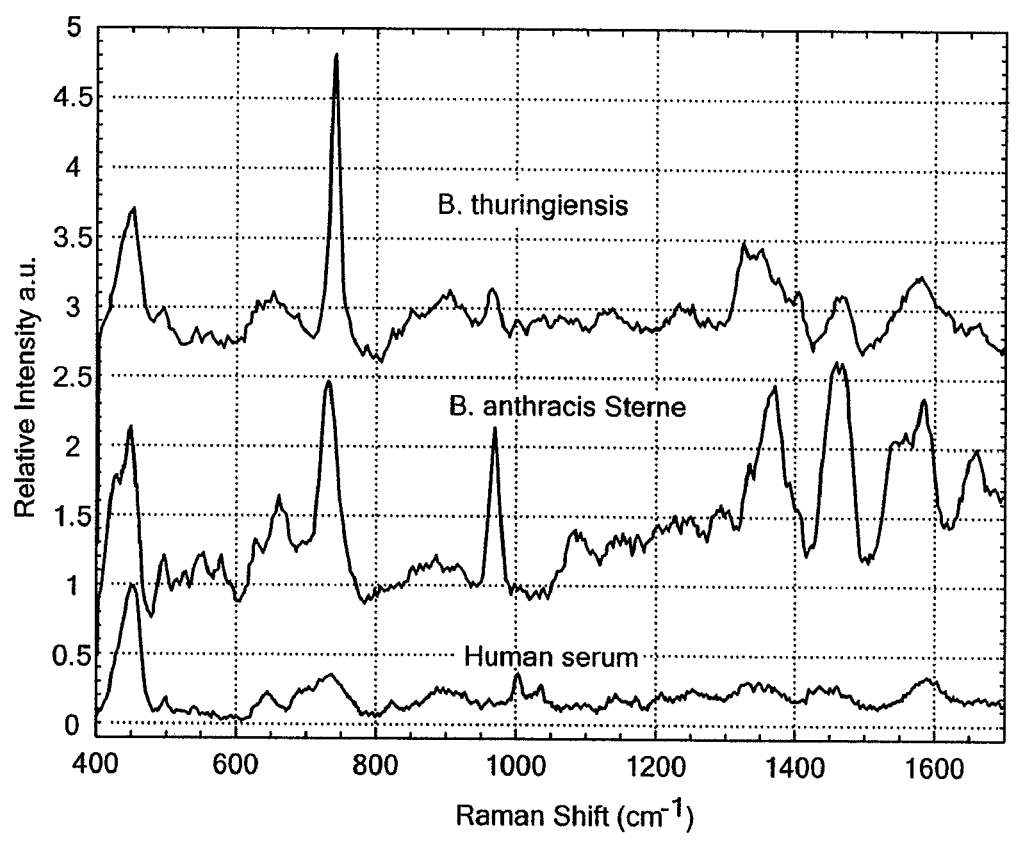

FIG. 12 shows SERS spectra for LB broth cultured *B. thuringiensis* and *B. anthracis* Sterne after admixing with human heparinized serum for about 1 to 3 hours. The admixtures were then placed on a substrate of the invention without additional washing. As shown, high quality vibrational signatures of these bacterial pathogens were obtained in the biological fluid. Although the effects of human heparinized serum on the vibrational signature of *B. anthracis* Sterne and *B. thuringiensis* were observable, reproducible species specific SERS spectral vibrational signatures were still obtained on the nanostructured substrate of the invention.

Figures 13A, 13B:
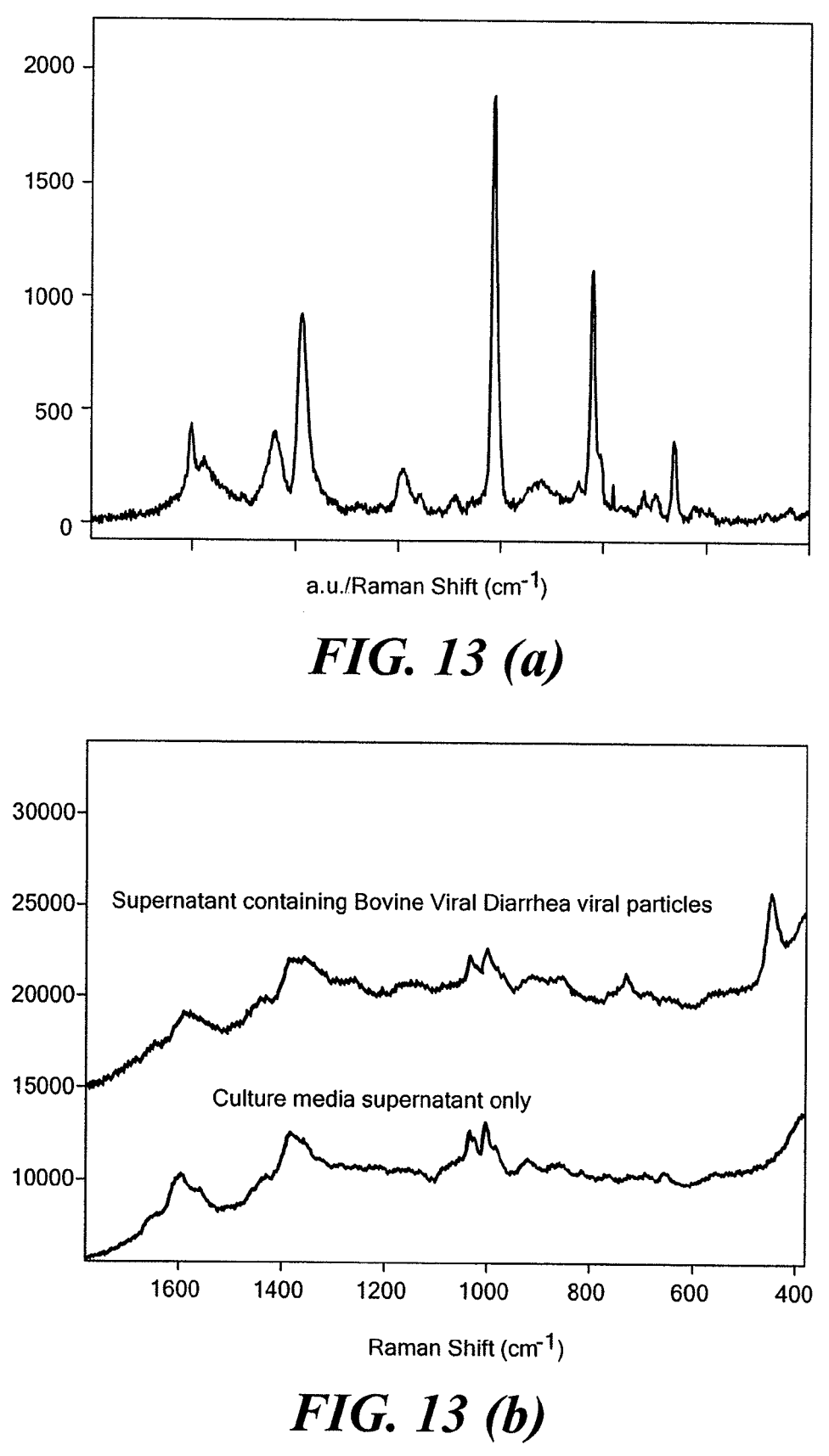

FIG. 13 (*a*) shows SERS spectra for *B. subtilis* spores provided via a nanostructured substrate of the invention. An aqueous suspension of *B. subtilis* spores were placed on the substrate. The substrate comprised a surface featuring substantially monodisperse-sized silver nanoparticles. The SERS spectra of these spores were readily observed in about 20 seconds with about 2 mW of 785 nm excitation.

FIG. 13 (*b*) shows SERS spectra of the supernatant from culture medium containing bovine viral diarrhea virus particles (upper trace) and a SERS spectrum for the corresponding culture medium supernatant of non-infected cells (lower trace) produced by using a nanostructured substrate of the invention. The nanostructured substrate comprising a surface featuring substantially monodisperse-sized gold nanoparticles. The differences between the upper and lower trace in FIG. 13 (*b*) are due to the viral pathogen.

While the invention has been described herein in conjunction with a preferred embodiment, a person of ordinary skill within the art, in view of the foregoing, can effect changes, substitutions of equivalents and other types of alterations to the nanostructured substrates for SERS set forth herein. Each embodiment described above can also have incorporated or otherwise included therewith such variations as disclosed in regard to any or all other embodiments. Thus, it is intended that protection granted by Letter Patent hereon be limited in breadth and scope only by definitions contained in the appended claims and any equivalents thereof.

Figure 14:
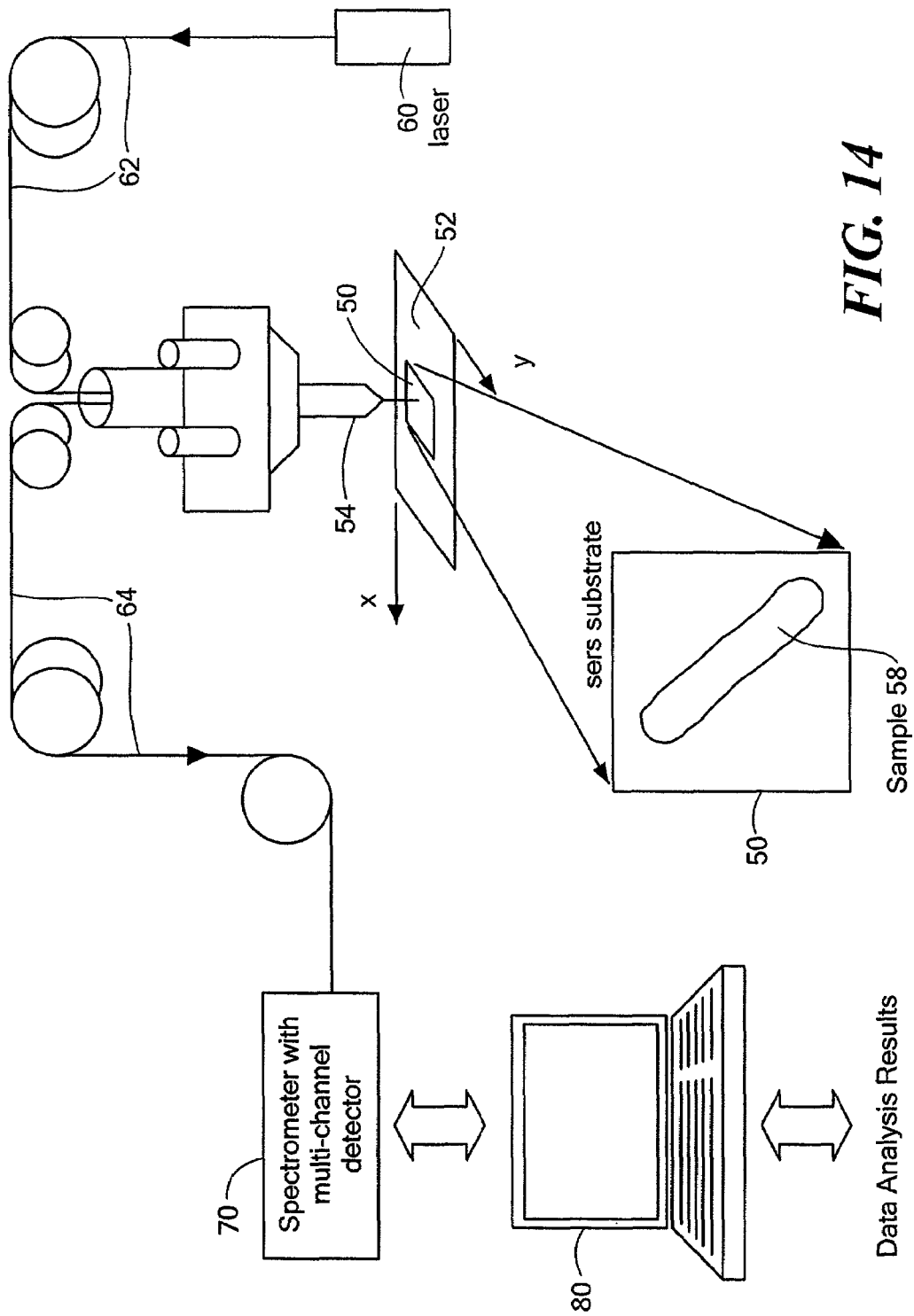
Figure 15:
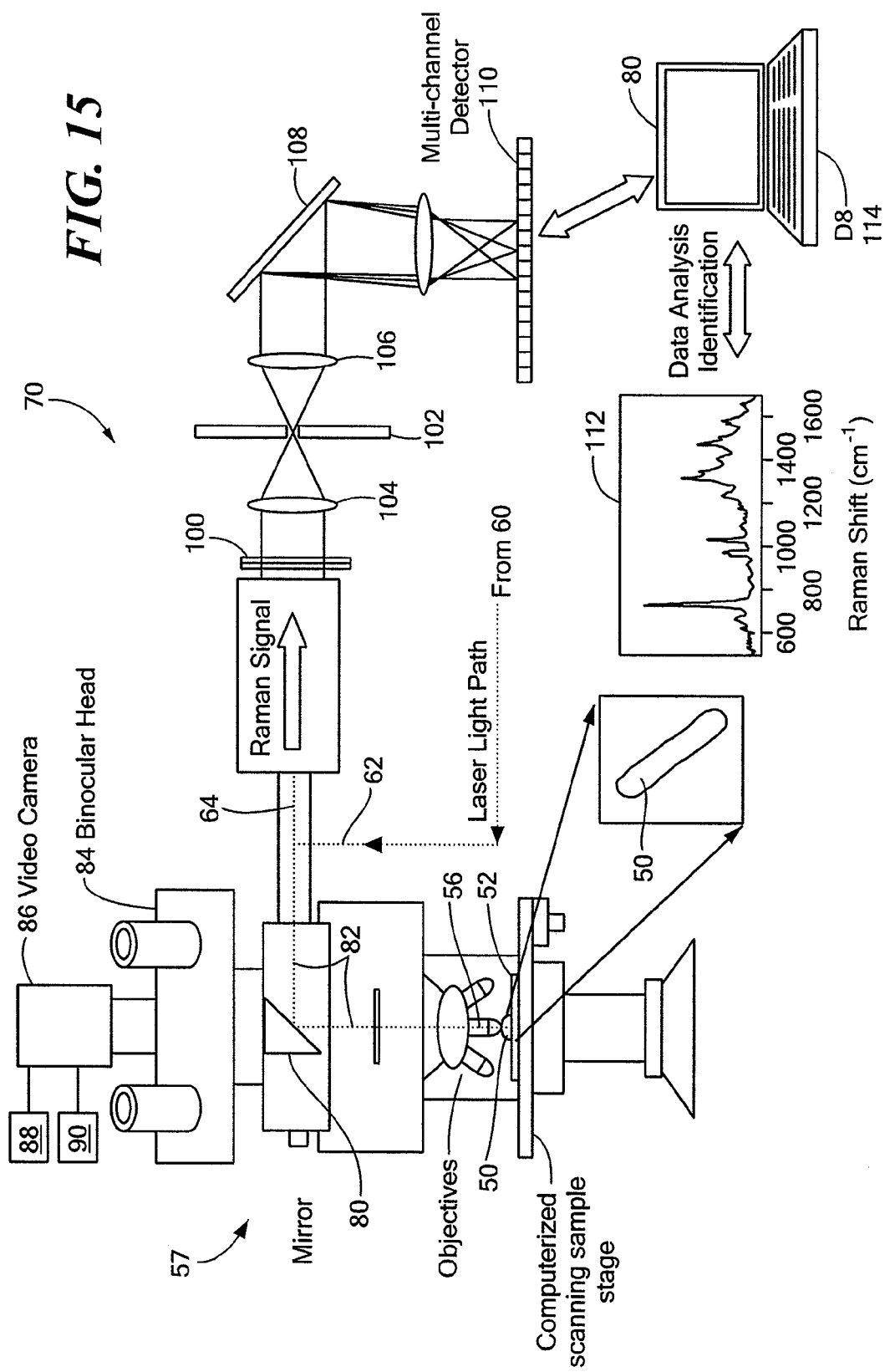
Figure 16:
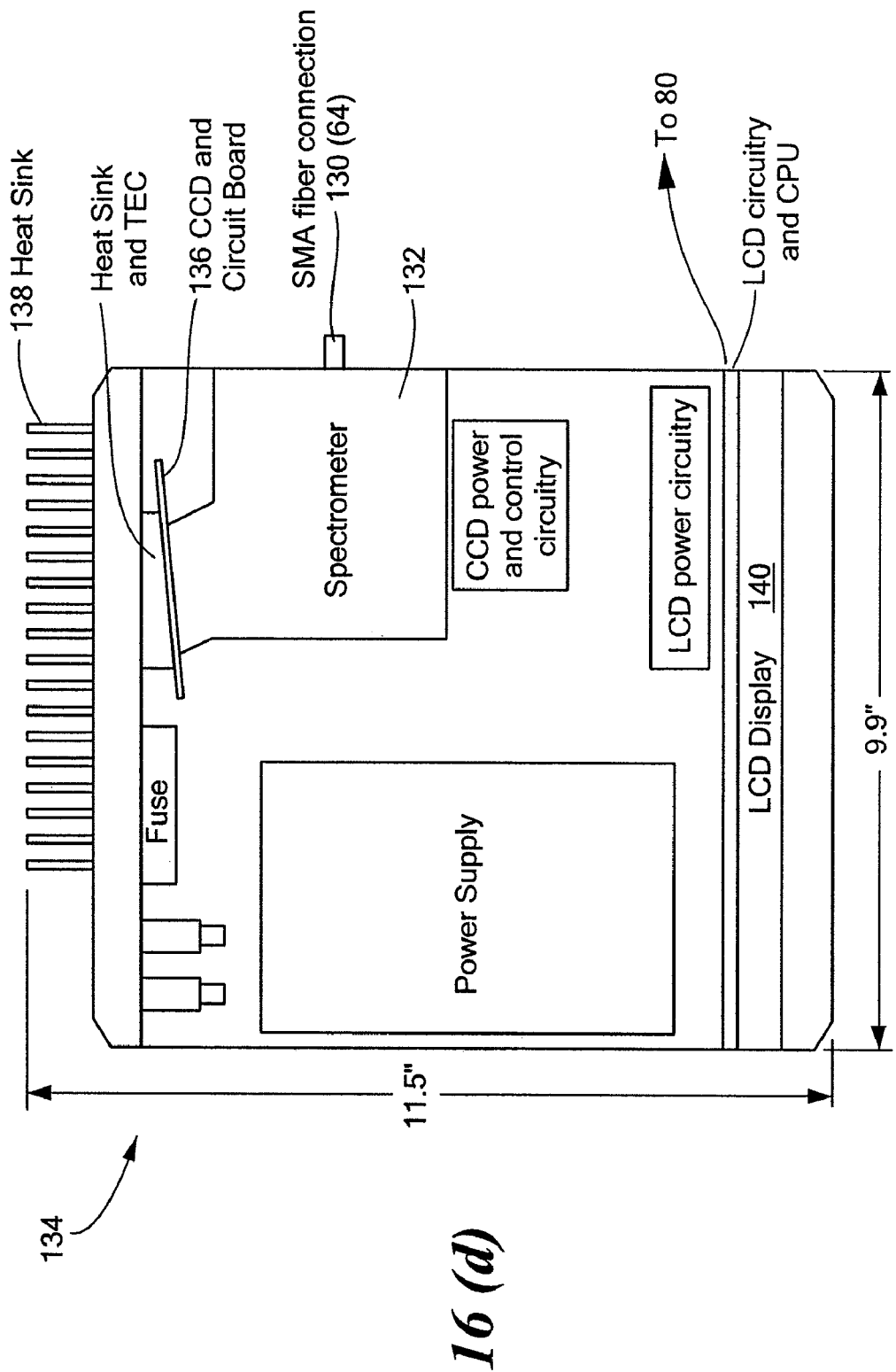

Instrumentation for producing a spectrographic signature of a specimen on one of the forgoing substrates is shown in FIGS. 14-16. FIG. 14 illustrates an analyzer of the invention in which one of the forgoing SERS substrates 50 is placed on a substrate 52 having X and Y motion. The substrate 50, typically having a bio-specimen 58 to be tested for type or other identity is within a field of view 54 of the objective (typically 40×) 56 of a microscope 57 such as a Raman or Renishaw Raman microscope. The sample stage can be spatially scanned automatically so that image recognition software can be used to identify specific pathogens in the field of view for SERS excitation and signal collection as described below.

Radiation from a source of defined wavelength such as a 1-25 mW laser 60 is applied through fiber optic cabling 62 to the microscope for illuminating the substrate 50 and any bio-specimen thereon. Raman scattered light, that is scattered light having a spectral content representative of vibrational excitation of any bio-specimen present, returns through the microscope onto fibers 64. The Raman spectrum representing signal on fibers 64 is directed to a spectrometer having a multi channel (eg. CCD) detector 70.

The spectrometer's multi-channel output representing the Raman spectrum characteristic of the bio-specimen under test is applied to a computer 80 which compares the that spectrum to spectra in a data base or library for comparison, allowing identification of a bio-specimen under test.

FIG. 15 shows in greater specificity the Raman analyzer of the invention. The radiation on fibers 62 and 64 enter and exit the microscope 57 via a reflector 80. The reflector 80 can be switched in or out of the laser light path 82 allowing in the out position light from the substrate 52 and any bio-specimen on it to be viewed by a binocular head 84 and/or viewed by a video camera for recording or display by units 88 and 90 respectively.

The Raman light on the fiber 64 is applied to the spectrometer 70 through a noise filter 100 and focused through a slit 102 by lenses 104 and 106 (de-collimating and collimating) onto a grating 108. In a laboratory embodiment of the invention the grating may be a 0.25M spectrograph. In a portable embodiment, discussed below, a 0.075M spectrograph is used. The spectrograph's grating 108 spatially separates the spectral content of the Raman light according to wavelength. The dispersed Raman spectrum is detected by a linear CCD array 110 that is coupled to computer 80. Computer 80 can display the SERS spectrum or Raman shift 112 and compare its waveform or data points to those in a data base 114 within the computer 80.

An embodiment of the invention for use in the field, particularly useful for investigating bio hazards from hostile acts of terrorists is shown in FIGS. 16*a*-16*d* illustrate the first of two units which is the source of the laser radiation and the resulting Raman signal. The laser and microscope are packaged in the unit 120, for example a modified Kaiser Raman probe head. The unit of FIG. 16a has an insertable slide holder 122 for a glass substrate 124 having the bio-specimen on a surface containing monodispersed-sized metal particles as taught above. The holder 122 is installed on a slide post 124 fixed in the instrument 120. An objective lens 128 focuses on the slide and metalized surface with any bio-specimen there.

The Raman signal from the Raman probe head 120 is applied over a fiber cable 130 to a spectrometer 132 packaged into a second portable unit 134. The spectrometer 130 applies its dispersedspectral signal to a CCD array 136 which is heat sinked at 138. The output of the CCD may be displayed on an LCD screen 140 and the corresponding signal is then available to computer 80 at an output 142.

Figure 17:
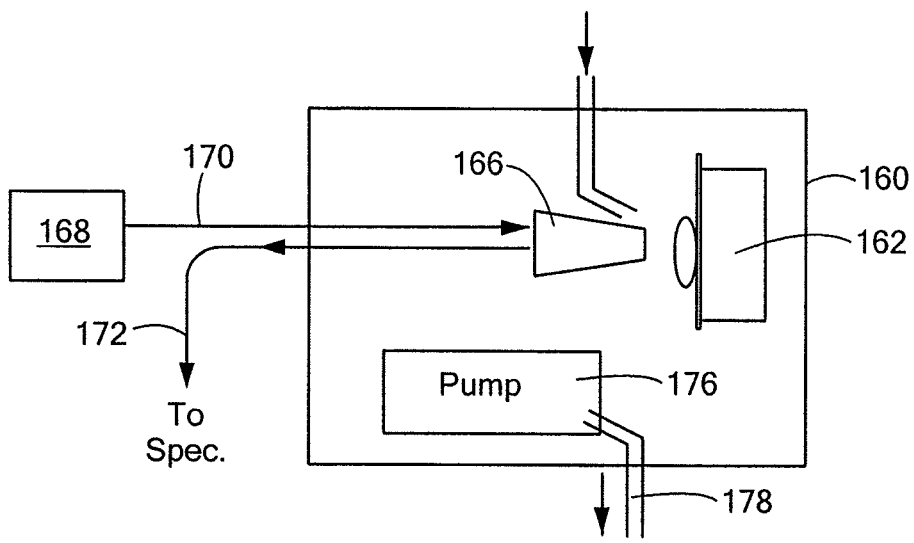
Figure 17:
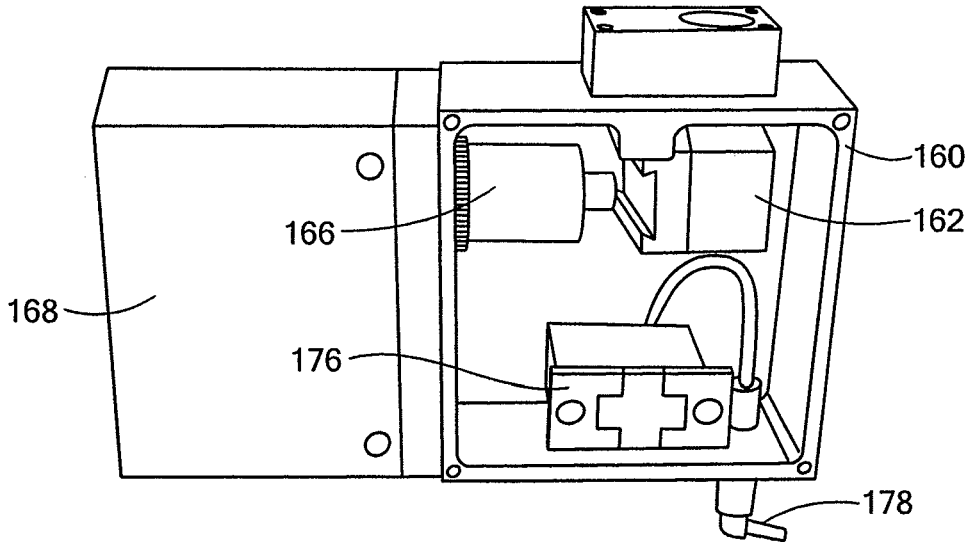

As shown in FIGS. 17a and 17b, the portable unit of FIG. 16a is provided with a fluid tight housing 160 in which the specimen mounting and scanning system 162 positions a specimen 164 in the optical axis of a microscope objective 166. The objective 166 is fed radiation as above from a laser 168 via fibers 170 and returning Raman radiation is sent to the spectrograph of FIG. 16d via fibers 172. The housing 160 has a gas or liquid intake port 174 to admit a gas or liquid environment to be analyzed as part of the specimen 162. In this case there is an exhaust pump 176 and exhaust vent 178 to draw the fluid in to the specimen area and flush it out after test.

FIG. 18 illustrates an optional functionality for the invention allowing recognition software in a processor 180 to respond to the video signal of the specimen area as provided above to drive the scanning specimen holder 184 holding the specimen 182 to move the specimen to or through the field of view of the objective 166.

REFERENCES

1. Olson et al., Characterization of silane-modified immobilized gold colloids as a substrate for surface-enhanced Raman spectroscopy, Anal. Chem., 2001, 73: pp. 4268-4276; Lee et al., Surface-enhanced Raman sensor for trace chemical detection in water, Proc. SPIE, 1999, 3857: pp. 76-84; Creighton et al., Metal colloids, in Surface enhanced Raman Scattering, 1982, Plenum: NYC, pp. 315-337; Volkan et al., A new surface-enhanced Raman scattering substrate based on silver nanoparticles in sol-gel, J. Raman Spect., 1999, 30: pp. 1057-1065; Premasiri et al., Determination of cyanide in waste water by low resolution surface enhanced Raman spectroscopy on sol-gel substrates, J. Raman Spect., 2001, 32: p. 919-922; Garcia-Rodriguez et al., Sol-gel $SiO_2$ films containing colloidal copper particles for surface enhanced Raman scattering of graphite, J. Raman Spect., 1998, 29: pp. 763-771; Akbarain et al., Porous sol-gel silicates containing gold particles as matrixes for surface-enhanced Raman spectroscopy, J. Raman Spect., 1996, 27: pp. 775-783; Lee et al., Silver-doped sol-gel films as the substrate for surface-enhanced Raman scattering, J. Raman Spect., 1997, 30: pp. 635-639; and Farquharson et al., Detection of bioagent signatures: A comparison of electrolytic and metal-doped sol-gel surface enhanced Raman media, Proc. SPIE, 2002, 4575: pp. 62-72.

2. Lee et al., Surface-enhanced Raman sensor for trace chemical detection in water, Proc. SPIE, 1999, 3857: pp. 76-84; Volkan et al., A new surface-enhanced Raman scattering substrate based on silver nanoparticles in sol-gel, J. Raman Spect., 1999, 30: pp. 1057-1065; Premasiri et al., Determination of cyanide in waste water by low resolution surface enhanced Raman spectroscopy on sol-gel substrates, J. Raman Spect., 2001, 32: p. 919; Garcia-Rodriguez et al., Sol-gel $SiO_2$ films containing colloidal copper particles for surface enhanced Raman scattering of graphite, J. Raman Spect., 1998, 29: pp. 763-771; Akbarain et al., Porous sol-gel silicates containing gold particles as matrixes for surface-enhanced Raman spectroscopy, J. Raman Spect., 1996, 27: pp. 775-783; Lee et al., Silver-doped sol-gel films as the substrate for surface-enhanced Raman scattering, J. Raman Spect., 1997, 30: pp. 635-639; and Farquharson et al., Detection of bioagent signatures: A comparison of electrolytic and metal-doped sol-gel surface enhanced Raman media, Proc. SPIE, 2002, 4575: pp. 62-72.

3. Lee et al., Surface-enhanced Raman sensor for trace chemical detection in water, Proc. SPIE, 1999, 3857: pp. 76-84; Volkan et al., A new surface-enhanced Raman scattering substrate based on silver nanoparticles in sol-gel, J. Raman Spect., 1999, 30: pp. 1057-1065; Premasiri et al., Determination of cyanide in waste water by low resolution surface enhanced Raman spectroscopy on sol-gel substrates, J. Raman Spect., 2001, 32: p. 919; Garcia-Rodriguez et al., Sol-gel $SiO_2$ films containing colloidal copper particles for surface enhanced Raman scattering of graphite, J. Raman Spect., 1998, 29: pp. 763-771; and Akbarain et al., Porous sol-gel silicates containing gold particles as matrixes for surface-enhanced Raman spectroscopy, J. Raman Spect., 1996, 27: pp. 775-783.

The invention claimed is:

1. A Raman scattering spectrographic analyzer comprising:
   a microscope having an objective with a field of view adapted to view specimens;
   means for supporting a substrate having monodispersed-sized metal particles thereon within the field of view of the microscope whereby specimens on one said substrate are within the field of view of said viewer;
   means for applying a defined wavelength of radiation through said microscope within said field of view and for returning radiation resulting from Raman scattering by specimens within said field of view;
   spectrographic means receiving Raman scattered radiation from said microscope and operative to provide a signal corresponding to the wavelength components in said Raman scattered radiation;
   means for analyzing said signal for identification of a specimen within said field of view; and
   brief case sized carrying means for said analyzer, said carrying means having means to accommodate one said substrate to place one said specimen within said field of view.

2. The analyzer of claim 1 further including means for scanning said field of view relative to substrate to cause said any specimen to traverse said field of view.

3. The analyzer of claim 2 wherein said scanning means includes means for spatially scanning said substrate in order to search for potential pathogens in applied specimens.

4. The analyzer of claim 3 wherein said analysing means includes library means for identifying bacteria as said substrate is spatially scanned.

5. The analyzer of claim 1 wherein said radiation applying means includes a laser.

6. The analyzer of claim 5 wherein said laser is a diode laser emitting at approximately 785 nm.

7. The analyzer of claim 6 wherein said laser has a low mw output.

8. The analyzer of claim 1 wherein said microscope is a Raman microscope.

9. The analyzer of claim 8 wherein said microscope has a $2\lambda$ resolution or better.

10. The analyzer of claim 1 wherein said spectrographic means includes a filter.

11. The analyzer of claim 1 wherein said spectrographic means includes a spectral dispersing element.

12. The analyzer of claim 11 wherein said dispersing element is a grating having a 0.075 M size or smaller.

13. The analyzer of claim 1 wherein said spectrographic means has a CCD sensor for detecting spectrally dispersed radiation.

14. The analyzer of claim 13 wherein said CCD sensor has a 7 $cm^{-1}$ or less resolution.

15. The analyzer of claim 1 wherein said means for analyzing includes computational means having a data library for comparing spectral signals from said spectrographic means against the signatures of known specimens.

16. The analyzer of claim 1 wherein said carrying means includes a first housing having therewith said means for applying radiation and a second housing having said spectrographic means therewith and an optical cable supplying radiation from said first housing to said second housing.

17. The analyzer of claim 1 wherein said specimen is selected from the group including specimens, gas phase specimens and liquid phase specimens or combinations thereof.

18. The analyzer of claim 1 further including means for flowing a fluid across said substrate in the field of view of said microscope.

19. A Raman scattering spectrographic analyzer comprising:
    a microscope having an objective with a field of view adapted to view specimens;
    means for supporting a substrate having monodispersed-sized metal particles thereon within the field of view of the microscope whereby specimens on one said substrate are within the field of view of said viewer;
    means for applying a defined wavelength of radiation through said microscope within said field of view and for returning radiation resulting from Raman scattering by specimens within said field of view;
    spectrographic means receiving Raman scattered radiation from said microscope and operative to provide a signal corresponding to the wavelength components in said Raman scattered radiation;
    means for analyzing said signal for identification of a specimen within said field of view; and a portable structure having:
        a first support structure for said radiation source, microscope and support; and
        a second support structure for said spectrographic means.

20. A method for performing a Raman scattering spectrographic analysis using a portable structure, the method comprising:
    providing a microscope having an objective with a field of view adapted to view specimens;
    supporting a substrate having monodispersed-sized metal particles thereon within the field of view of the microscope whereby specimens on one said substrate are within the field of view of said viewer;
    applying a defined wavelength of radiation through said microscope within said field of view and for returning radiation resulting from Raman scattering by specimens within said field of view by using a radiation source that is supported by a first support structure that is disposed in the portable structure;
    receiving Raman scattered radiation from said microscope using a spectrographic means that is supported by a second support structure that is disposed in the portable structure;
    generating a signal corresponding to the wavelength components in said Raman scattered radiation using the spectrographic means; and
    analyzing said signal for identification of a specimen within said field of view.

21. A method for field identification of a bio specimen comprising the steps of:
    conveying to a remote field location a Raman scattering spectrographic analyzer comprising:
    a microscope having an objective with a field of view adapted to view specimens;
    means for supporting a substrate having monodispersed-sized metal particles thereon within the field of view of the microscope whereby specimens on one said substrate are within the field of view of said viewer;
    means for applying a defined wavelength of radiation through said microscope within said field of view and for returning radiation resulting from Raman scattering by specimens within said field of view;
    spectrographic means receiving Raman scattered radiation from said microscope and operative to provide a signal corresponding to the wavelength components in said Raman scattered radiation;
    means for analyzing said signal for identification of a specimen within said field of view; and
    brief case sized carrying means for said analyzer, said carrying means having means to accommodate one said substrate to place one said specimen within said field of view; and
    performing spectrographic analysis of said bio specimen at said remote field location with said Raman scattering spectrographic analyzer.

* * * * *

UNITED STATES PATENT AND TRADEMARK OFFICE
CERTIFICATE OF CORRECTION

PATENT NO. : 7,595,872 B2  Page 1 of 1
APPLICATION NO. : 11/792007
DATED : September 29, 2009
INVENTOR(S) : W. Ranjith Premasiri et al.

It is certified that error appears in the above-identified patent and that said Letters Patent is hereby corrected as shown below:

On the title page, item (75) Inventors, "Lexington" should read -- Concord --.

Signed and Sealed this

Twenty-ninth Day of June, 2010

David J. Kappos
*Director of the United States Patent and Trademark Office*